United States Patent
Franz et al.

(10) Patent No.: US 9,816,953 B2
(45) Date of Patent: Nov. 14, 2017

(54) MICROMECHANICAL MOISTURE SENSOR DEVICE, CORRESPONDING MANUFACTURING METHOD, AND MICROMECHANICAL SENSOR SYSTEM

(71) Applicant: Robert Bosch Gmbh, Stuttgart (DE)

(72) Inventors: Jochen Franz, Reutlingen (DE); Uwe Schiller, Tuebingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 516 days.

(21) Appl. No.: 14/304,394

(22) Filed: Jun. 13, 2014

(65) Prior Publication Data

US 2014/0366630 A1 Dec. 18, 2014

(30) Foreign Application Priority Data

Jun. 18, 2013 (DE) .................... 10 2013 211 378

(51) Int. Cl.
*G01N 19/00* (2006.01)
*G01N 27/22* (2006.01)
*G01N 27/04* (2006.01)

(52) U.S. Cl.
CPC ......... *G01N 27/223* (2013.01); *G01N 27/048* (2013.01)

(58) Field of Classification Search
CPC .. G01N 27/223; G01N 27/225; G01N 27/121; G01N 25/64; G01N 25/56; G01N 33/246; G01N 25/60; G01N 25/68; G01N 27/226; G01N 19/10; G01N 21/3504; G01N 33/0031; G01N 33/225; B60H 1/00785; B60S 1/0822; H01G 4/30; H01G 13/00; H01G 13/006

USPC .......... 73/335.04, 335.05, 73, 335.02, 336.5; 702/24; 338/35; 257/48; 428/323; 361/286; 505/100; 29/25.42; 324/664
See application file for complete search history.

(56) References Cited

U.S. PATENT DOCUMENTS

| | | | | | |
|---|---|---|---|---|---|
| 4,893,214 | A | * | 1/1990 | Nishiwaki | G01N 27/225 29/25.42 |
| 6,647,782 | B2 | * | 11/2003 | Toyoda | G01N 27/225 257/253 |
| 7,332,995 | B2 | * | 2/2008 | Arisaka | G01N 27/225 338/35 |
| 7,340,952 | B2 | * | 3/2008 | Tanida | G01N 27/225 361/286 |
| 2002/0040598 | A1 | * | 4/2002 | Sugaya | G01N 27/121 73/335.02 |

(Continued)

FOREIGN PATENT DOCUMENTS

DE 198 53 135 5/2000
DE 199 17 717 11/2000

*Primary Examiner* — John Fitzgerald
*Assistant Examiner* — Truong D Phan
(74) *Attorney, Agent, or Firm* — Norton Rose Fulbright US LLP; Gerard Messina

(57) ABSTRACT

A micromechanical moisture sensor device includes: a substrate having a front side and a rear side; an interdigital printed conductor track arrangement provided above and/or below the front side of the substrate; and a moisture-sensitive polymer layer situated above and in the gaps of the interdigital printed conductor track arrangement. The moisture-sensitive polymer layer extends below the front side into the substrate.

19 Claims, 3 Drawing Sheets

(56) References Cited

U.S. PATENT DOCUMENTS

| | | | | |
|---|---|---|---|---|
| 2002/0190840 A1* | 12/2002 | Fujita | .................... | G01N 27/121 |
| | | | | 338/35 |
| 2006/0096371 A1* | 5/2006 | Isogai | ................... | G01N 27/223 |
| | | | | 73/335.04 |
| 2006/0238290 A1* | 10/2006 | Arisaka | ................ | G01N 27/225 |
| | | | | 338/35 |
| 2009/0108852 A1* | 4/2009 | Alimi | .................... | G01N 27/223 |
| | | | | 324/664 |
| 2012/0125114 A1* | 5/2012 | Stewart | ................... | G01L 9/065 |
| | | | | 73/721 |
| 2012/0253691 A1* | 10/2012 | Graf | ..................... | G01N 27/223 |
| | | | | 702/24 |
| 2014/0291677 A1* | 10/2014 | Le Neel | ............. | H01L 25/0652 |
| | | | | 257/48 |

* cited by examiner

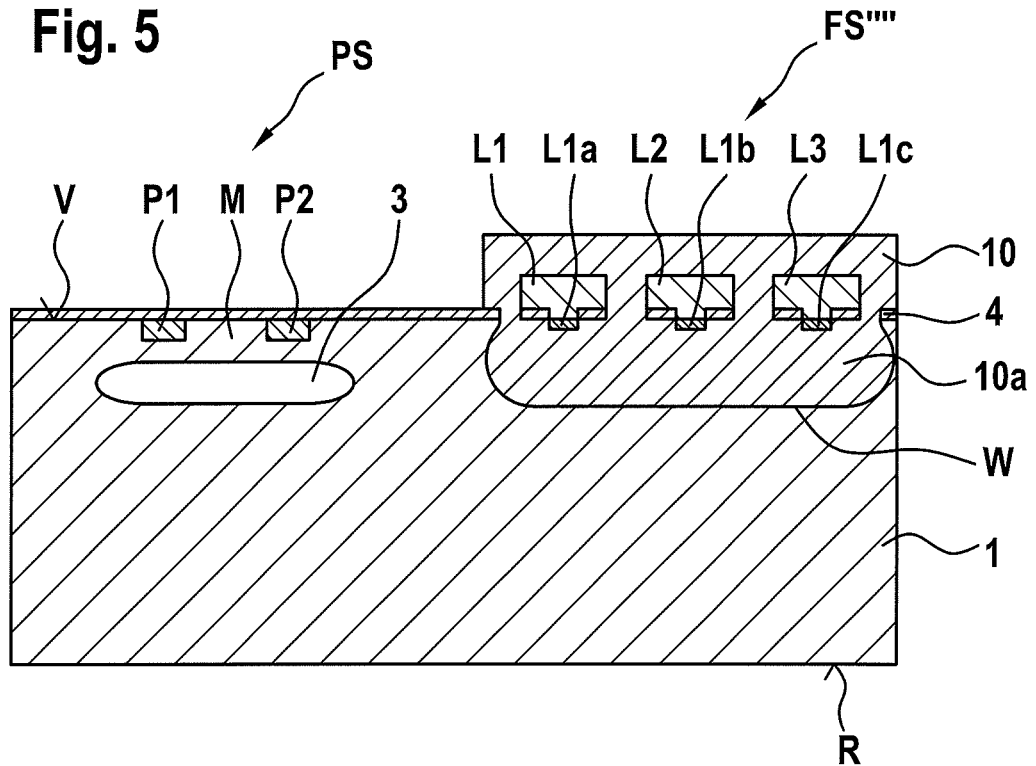
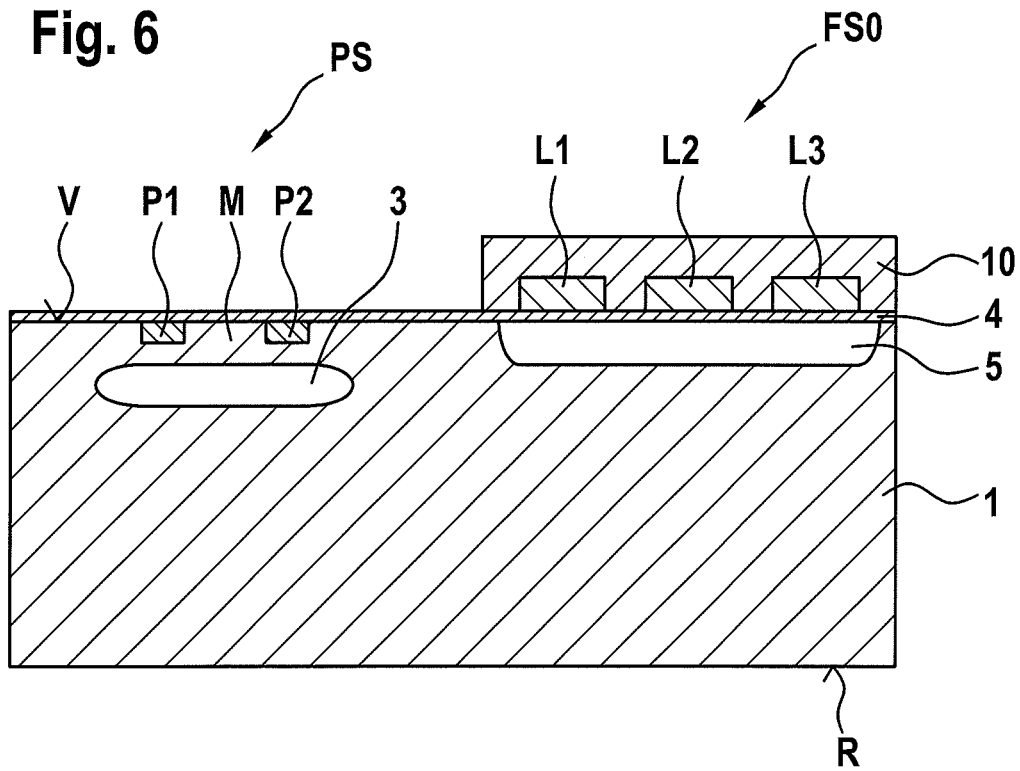

MICROMECHANICAL MOISTURE SENSOR DEVICE, CORRESPONDING MANUFACTURING METHOD, AND MICROMECHANICAL SENSOR SYSTEM

BACKGROUND OF THE INVENTION

1. Field of the Invention

The present invention relates to a micromechanical moisture sensor device, a corresponding manufacturing method, and a micromechanical sensor system.

2. Description of the Related Art

The present invention and the underlying problem are explained based on silicon-based micromechanical moisture sensors and pressure sensors, although they are in principle applicable to any micromechanical moisture sensor devices.

Micromechanical pressure sensors have become standard sensors in both the automotive field and the consumer application field. Moisture sensors are currently gaining importance for ascertaining the additional measured variable of moisture.

At the present time, both sensor types are available as single sensors in a micromechanical design and are applied in stand-alone packages. Each sensor has the same access to the media surroundings and thus sees the same surrounding conditions. However, it is in principle also conceivable to integrate both sensor types in the same substrate, as explained below based on FIG. 6.

FIG. 6 is a schematic cross-sectional representation of a micromechanical moisture sensor device known from published German patent application document DE 199 17 717 A1 in combination with a pressure sensor device known from published German patent application document DE 198 53 135 A1.

In FIG. 6, reference numeral 1 refers to a silicon substrate having a front side V and a rear side R, in which a moisture sensor FS0 and a pressure sensor PS are integrated side by side.

Moisture sensor FS0 has a potential well 5, for example, a p-well, situated in the substrate. An insulating layer 4, for example, made of silicon nitride, is applied on front side V of substrate 1. An interdigital printed conductor track arrangement including printed conductor track sections L1, L2, and L3 is applied above potential well 5 and on insulating layer 4, on which a moisture-sensitive polymer layer 10 is situated, which extends into the gaps between the printed conductor track sections L1, L2, L3 and thus surrounds them. Not shown in FIG. 6 is an optional electrode, for example, a gold electrode, which is provided on moisture-sensitive polymer layer 10.

Using a capacitance measurement, it is possible to determine the moisture content of moisture-sensitive polymer layer 10, for example, via a simple capacitance measurement, a half-bridge measurement, or a full-bridge measurement, in which in the latter measurement, multiple interdigital printed conductor track arrangements would have to be provided side by side on insulating layer 4.

Pressure sensor PS according to FIG. 6 has a cavern 3 situated in substrate 1, above which a diaphragm area M is formed. Piezoresistive resistors P1, P2 are provided in or on diaphragm area M, which change their resistance under deformation of diaphragm area M and thus are able to provide a signal for ascertaining the applied pressure.

BRIEF SUMMARY OF THE INVENTION

The idea underlying the present invention is increasing the moisture sensitivity by extending the moisture-sensitive polymer layer between the capacitance fingers into the substrate.

In the case of a sensor system including a moisture sensor device according to the present invention in combination with a pressure sensor device known per se, it is possible to achieve synergy effects in the evaluation of the sensor signals and in the manufacturing method. By integrating both sensor functions in one substrate, it is possible to provide a single package and a single combined evaluation unit. Because the media access and the requirements for both sensor types are identical, the packaging of integrated circuits may be simplified considerably. In addition, such a monolithic integration has considerable cost advantages compared to discrete sensors.

According to one preferred refinement, the moisture-sensitive polymer layer extends into trenches in the substrate situated in the gaps of the interdigital printed conductor track arrangement. Such trenches may be manufactured in a simple manner using a trench etching process, in which the interdigital printed conductor track arrangement may act as a self-aligned mask.

According to another preferred refinement, the moisture-sensitive polymer layer extends into a well in the substrate which is filled with the moisture-sensitive polymer layer and which is situated below the interdigital printed conductor track arrangement. The interdigital printed conductor track arrangement is thus surrounded on all sides by the moisture-sensitive polymer layer, thereby increasing the sensitivity.

According to another preferred refinement, the interdigital printed conductor track arrangement has a first interdigital printed conductor track arrangement provided above the front side of the substrate and a second interdigital printed conductor track arrangement parallel to it provided below the front side of the substrate, which are arranged one above the other in such a way that they are electrically connected to each other. The capacitance is thereby increased and thus also the sensitivity.

BRIEF DESCRIPTION OF THE DRAWINGS

FIG. 5 shows a schematic cross-sectional representation of a micromechanical moisture sensor device according to a fifth specific embodiment of the present invention.

FIG. 6 shows a schematic cross-sectional representation of a micromechanical moisture sensor device known from DE 199 17 717 A1 in combination with a pressure sensor device known from DE 198 53 135 A1.

DETAILED DESCRIPTION OF THE INVENTION

Figure 1:
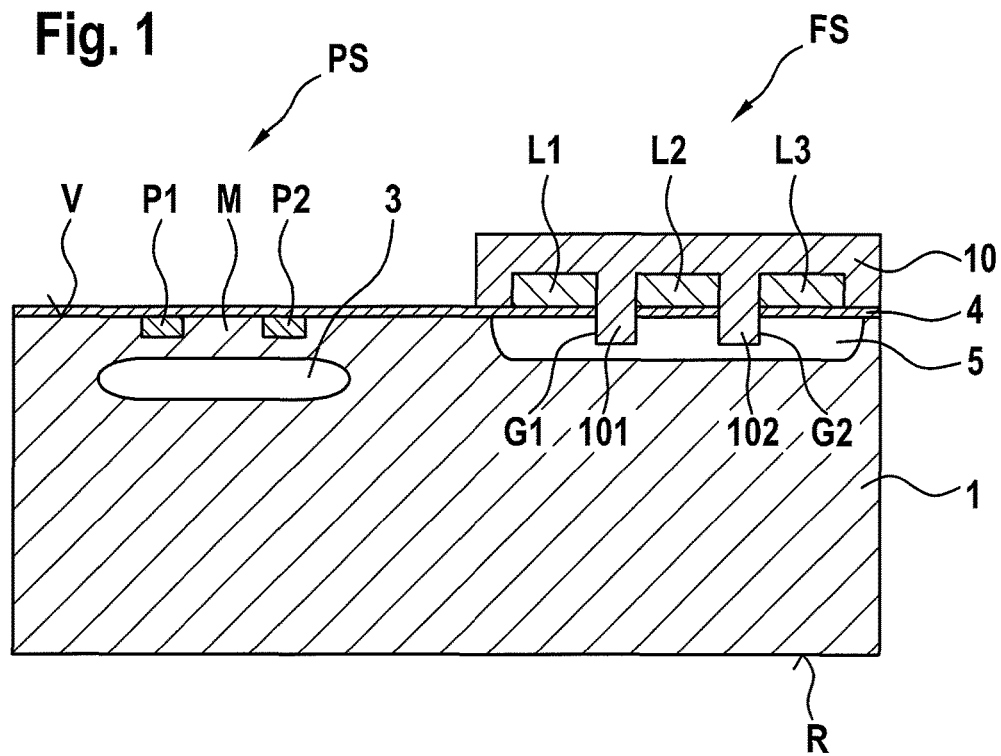
FIG. 1 shows a schematic cross-sectional representation of a micromechanical moisture sensor device according to one first specific embodiment of the present invention.

In the figures, identical reference numerals refer to identical or functionally identical elements.

FIG. 1 is a schematic cross-sectional representation of a micromechanical moisture sensor device according to one first specific embodiment of the present invention.

According to FIG. 1, a moisture sensor device FS according to the first specific embodiment and a pressure sensor device PS are integrated side by side in the same substrate 1.

The structure of pressure sensor device PS is just as described above with reference to FIG. 6.

Moisture sensor device FS differs from the structure already described above with reference to FIG. 6 in that moisture-sensitive polymer layer 10 extends into substrate 1 below front side V. For this purpose, trenches G1, G2 are etched into substrate 1 or into potential well 5 situated in it, which is optional, in the gaps between printed conductor track sections L1, L2, L3, via a conventional trench etching process. In this etching process, printed conductor track sections L1, L2, L3 in the digital printed conductor track arrangement may be used as self-aligned masks. In this case, the surrounding area must be protected using a corresponding additional mask.

After forming trenches G1, G2, the deposition and structuring are carried out of moisture-sensitive polymer layer 10, which thus fills the trenches between printed conductor track sections L1, L2, L3 in sections 101, 102 and thereby extends into substrate 1. This arrangement makes it possible to increase the sensitivity of moisture sensor device FS.

Figure 2:
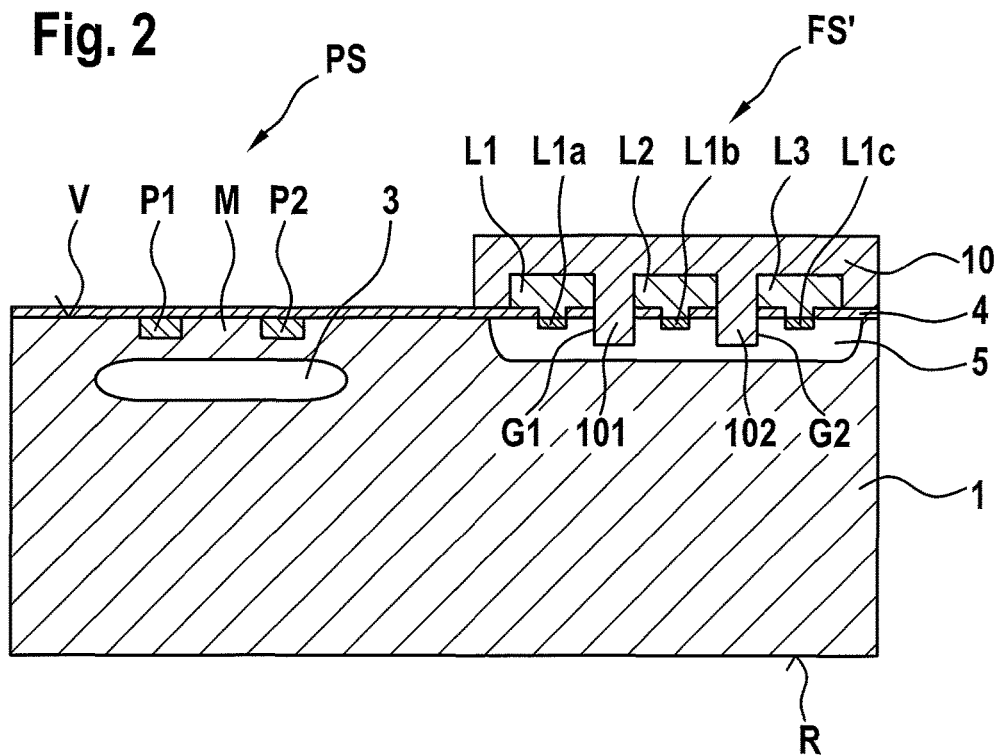
FIG. 2 shows a schematic cross-sectional representation of a micromechanical moisture sensor device according to one second specific embodiment of the present invention.

FIG. 2 is a schematic cross-sectional representation of a micromechanical moisture sensor device according to one second specific embodiment of the present invention.

In comparison to the first specific embodiment, in the second specific embodiment according to FIG. 2, moisture sensor device FS' is modified in such a way that an additional interdigital printed conductor track arrangement L1a, L1b, L1c is provided in potential well 5, which runs in parallel to interdigital printed conductor track arrangement L1, L2, L3 and which is electrically connected to it via contact holes in insulating layer 4, through which they are directly connected. Additional digital printed conductor track arrangement L1a, L1b, L1c may be introduced into potential well 5, for example, using a diffusion process.

The remaining structure of the second specific embodiment is analogous to the first specific embodiment, it being preferred that areas 101, 102 of moisture-sensitive polymer layer 10 extend further into substrate 1 than printed conductor track sections L1a, L1b, L1c of the additional interdigital printed conductor track arrangement, in order to shield stray fields.

Figure 3:
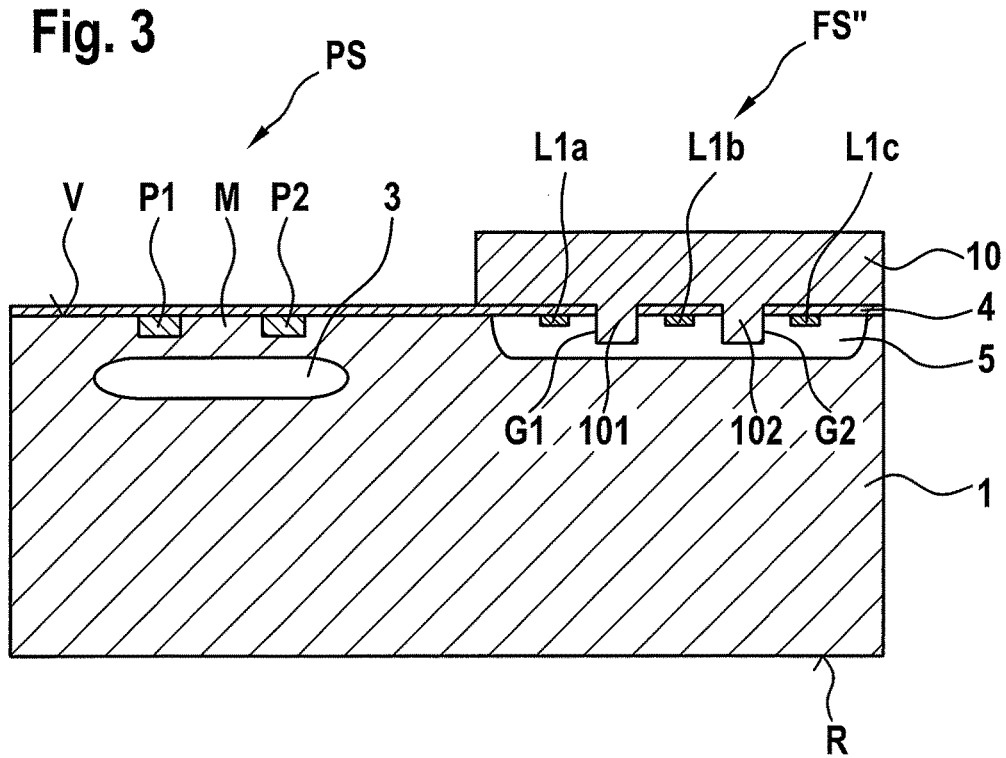
FIG. 3 shows a schematic cross-sectional representation of a micromechanical moisture sensor device according to one third specific embodiment of the present invention.

FIG. 3 is a schematic cross-sectional representation of a micromechanical moisture sensor device according to one third specific embodiment of the present invention.

In the third specific embodiment according to FIG. 3, in comparison to the second specific embodiment, interdigital printed conductor track arrangement L1, L2, L3 is omitted in moisture sensor device FS", and only interdigital printed conductor track arrangement L1a, L1b, L1c situated in potential well 5 is provided. Otherwise, the structure is identical to the second specific embodiment described above.

Figure 4:
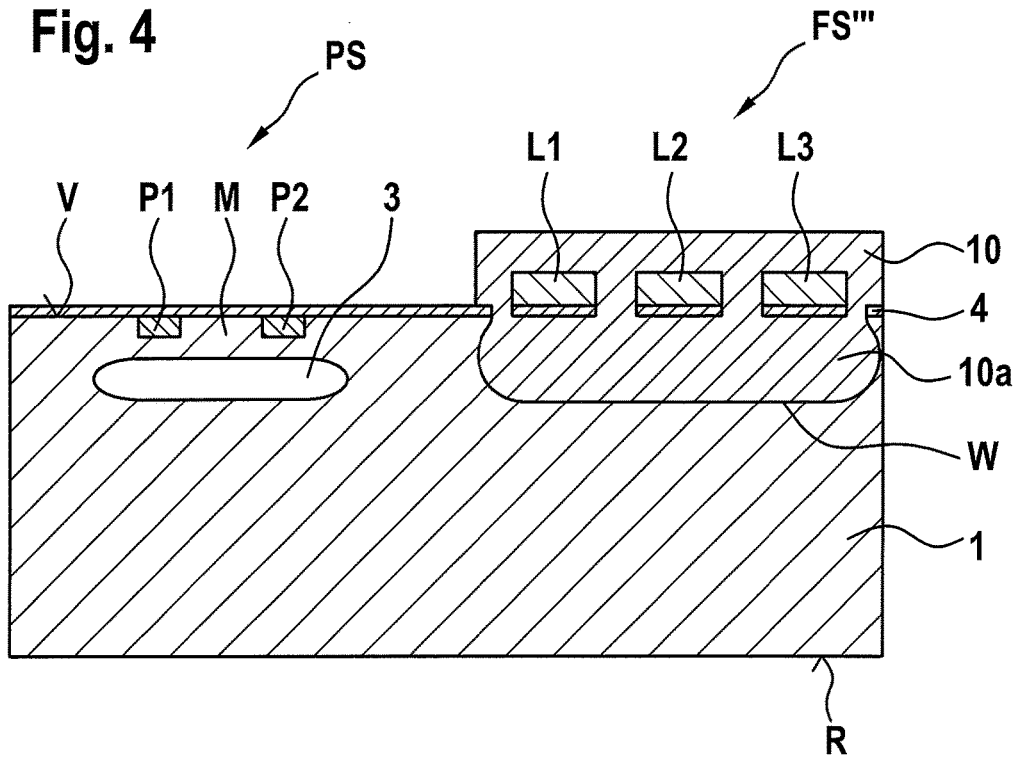
FIG. 4 shows a schematic cross-sectional representation of a micromechanical moisture sensor device according to one fourth specific embodiment of the present invention.

FIG. 4 is a schematic cross-sectional representation of a micromechanical moisture sensor device according to one fourth specific embodiment of the present invention.

In the fourth specific embodiment according to FIG. 4, potential well 5 is omitted. Instead, a well W is situated in the substrate below interdigital printed conductor track arrangement L1, L2, L3, which is completely filled with the moisture-sensitive polymer layer 10, 10a, the portion of moisture-sensitive polymer layer 10 situated in the substrate being indicated by reference numeral 10a. It is thus possible to surround interdigital printed conductor track arrangement L1, L2, L3 of relevant moisture sensor device FS''' from all sides with moisture-sensitive polymer layer 10, 10a, thus further increasing the sensitivity of moisture sensor device FS'''. The manufacture of well W may simultaneously be carried out for the generation of cavity 3 for the pressure sensor, which is economically reasonable in process-related terms.

FIG. 5 is a schematic cross-sectional representation of a micromechanical moisture sensor device according to one fifth specific embodiment of the present invention.

In comparison to the fourth specific embodiment, in the fifth specific embodiment, additional interdigital printed conductor track arrangement L1a, L1b, L1c is provided, which is in electrical communication with interdigital printed conductor track arrangement L1, L2, L3 and runs in parallel to it. Such an arrangement may be achieved via a correspondingly controlled etching process during the formation of well W. Otherwise, the fifth specific embodiment is structured analogously to the fourth specific embodiment.

Although the moisture sensor device is represented in combination with a pressure sensor device in the specific embodiment described above, it is also possible to use the moisture sensor device as a single sensor. However, the combination is recommended in particular due to process-related synergy effects.

The monolithic integration of the above-described sensor systems of pressure sensor device PS and moisture sensor device FS, FS', FS", FS''', FS"" side by side is relatively simple to implement. A direct mechanical interaction with the pressure sensor bridge circuit (not shown) may be minimized via appropriate spacing. Aluminum structures should also be placed at a distance from diaphragm area M in order to avoid thermal hystereses for pressure sensor device PS. Bonding pads for making contact with the sensor system may be situated on different sides or on the same side of the sensor devices. Depending on the accuracy requirement, the complexity of the capacitors for the moisture sensor device may also be carried out as a half bridge or a full bridge. In simple capacitance structures, required reference capacitors must be provided in the evaluation circuit, if necessary.

The integration of piezoresistive resistors, capacitors, and, for example, additional temperature diodes makes it necessary to provide different signal conversions in the evaluation circuit. If, for example, a capacitive pressure sensor is used instead of the piezoresistive pressure sensor, an additional simplification of the evaluation circuit thus results. The evaluation circuit may contain the required signal converters, which route their signals via a multiplexer circuit to an A/D converter whose output signal is fed to a data processing device. Known packages may be used to provide a sensor package for the above-described sensor systems. The sensor chip including the sensor system and the ASIC chip including the evaluation circuit may also be arranged on a shared substrate, in which the sensor chip is able to be protected via a metal cap having media access. An additional media passivation is not carried out in this case.

What is claimed is:

1. A micromechanical moisture sensor device, comprising:
   a substrate having a front side and a rear side;
   an interdigital printed conductor track arrangement provided at least one of above and below the front side of the substrate; and a moisture-sensitive polymer layer situated (i) above the interdigital printed conductor track arrangement and (ii) in gaps of the interdigital printed conductor track arrangement;

wherein the moisture-sensitive polymer layer extends into the substrate below the front side.

2. The micromechanical moisture sensor device as recited in claim 1, wherein the moisture-sensitive polymer layer extends into trenches in the substrate situated in the gaps of the interdigital printed conductor track arrangement.

3. The micromechanical moisture sensor device as recited in claim 1, wherein the moisture-sensitive polymer layer extends into a well in the substrate which is (i) filled with the moisture-sensitive polymer layer and (ii) situated below the interdigital printed conductor track arrangement.

4. The micromechanical moisture sensor device as recited in claim 1, wherein the interdigital printed conductor track arrangement has a first interdigital printed conductor track arrangement provided above the front side of the substrate and a second interdigital printed conductor track arrangement parallel to the first interdigital printed conductor track arrangement and provided below the front side of the substrate, and wherein the first and second interdigital printed conductor track arrangements are arranged one above the other and electrically connected to each other.

5. The micromechanical moisture sensor device as recited in claim 1, wherein a potential well is formed in the substrate, the interdigital printed conductor track arrangement is arranged over the potential well, and the moisture-sensitive polymer layer extends into the potential well.

6. The micromechanical moisture sensor device as recited in claim 5, wherein the potential well is a p-well.

7. The micromechanical sensor system as recited in claim 1, further comprising:
a pressure sensor device integrated into the substrate.

8. The micromechanical sensor system as recited in claim 7, wherein the pressure sensor device has a diaphragm area including at least one piezoresistor provided one of (i) in the diaphragm area or (ii) on the diaphragm area.

9. The micromechanical sensor system as recited in claim 7, wherein the pressure sensor device is a capacitive pressure sensor device.

10. The micromechanical moisture sensor device as recited in claim 1, further comprising an insulating layer on the front side of the substrate, wherein the moisture-sensitive polymer layer extends into and through the insulating layer.

11. The micromechanical moisture sensor device as recited in claim 10, wherein the interdigital printed conductor track arrangement is provided on the insulating layer.

12. The micromechanical moisture sensor device as recited in claim 11, wherein the insulating layer is formed of silicon nitride.

13. A method for manufacturing a micromechanical moisture sensor device, comprising:
providing a substrate having a front side and a rear side;
forming an interdigital printed conductor track arrangement provided at least one of above and below the front side of the substrate; and
forming a moisture-sensitive polymer layer situated (i) above the interdigital printed conductor track arrangement and (ii) in gaps of the interdigital printed conductor track arrangement, wherein the moisture-sensitive polymer layer extends into the substrate below the front side.

14. The method as recited in claim 13, wherein trenches are formed in the substrate in the gaps of the interdigital printed conductor track arrangement and are filled with the moisture-sensitive polymer layer such that the moisture-sensitive polymer layer extends into the trenches in the substrate.

15. The method as recited in claim 13, wherein a well is formed in the substrate below the interdigital printed conductor track arrangement and is filled with the moisture-sensitive polymer layer such that the moisture-sensitive polymer layer extends into the well in the substrate.

16. The method as recited in claim 13, wherein the interdigital printed conductor track arrangement is configured to include a first interdigital printed conductor track arrangement provided above the front side of the substrate and a second interdigital printed conductor track arrangement parallel to the first interdigital printed conductor track arrangement and provided below the front side of the substrate, and wherein the first and second interdigital printed conductor track arrangements are arranged one above the other and electrically connected to each other.

17. The method as recited in claim 13, further comprising:
providing a pressure sensor device integrated into the substrate.

18. The method as recited in claim 13, further comprising forming trenches in a plane below the interdigital printed conductor track arrangement, wherein lateral positions of the trenches are between lateral positions of conductor tracks of the interdigital printed conductor track arrangement, the forming of the trenches includes etching using the interdigital printed conductor track arrangement as a mask, and the forming of the moisture-sensitive polymer layer includes depositing moisture-sensitive polymer material in the trenches.

19. A micromechanical moisture sensor device comprising:
a substrate having a front side and a rear side;
an interdigital printed conductor track arrangement provided at least one of above and below the front side of the substrate; and
a moisture-sensitive polymer layer situated (i) above the interdigital printed conductor track arrangement and (ii) in gaps of the interdigital printed conductor track arrangement
wherein the moisture-sensitive polymer layer extends from above the interdigital printed conductor track arrangement into the substrate below the front side and below a lowest edge of the interdigital printed conductor track arrangement.

* * * * *